United States Patent [19]

Uchiyama

[11] Patent Number: 4,476,876
[45] Date of Patent: Oct. 16, 1984

[54] ELECTRONIC SPHYGMOMANOMETER

[75] Inventor: Taizo Uchiyama, Fujinomiya, Japan

[73] Assignee: Terumo Kabushiki Kaisha, Tokyo, Japan

[21] Appl. No.: 400,933

[22] Filed: Jul. 22, 1982

[30] Foreign Application Priority Data

Aug. 1, 1981 [JP] Japan .................................. 56-121039

[51] Int. Cl.³ .............................................. A61B 5/02
[52] U.S. Cl. .................................... 128/682; 128/681
[58] Field of Search .................. 128/672, 677, 680–683

[56] References Cited

U.S. PATENT DOCUMENTS

| | | | |
|---|---|---|---|
| 3,349,763 | 10/1967 | Clements, Jr. et al. | 128/680 |
| 3,533,401 | 10/1970 | Streu | 128/682 |
| 3,878,834 | 4/1975 | Sanderson | 128/680 |
| 4,058,117 | 11/1977 | Kaspari | 128/682 |
| 4,137,907 | 2/1979 | Jansen et al. | 128/681 |
| 4,188,955 | 2/1980 | Sakamoto et al. | 128/680 |
| 4,214,589 | 7/1980 | Sakamoto et al. | 128/680 |
| 4,216,779 | 8/1980 | Squires et al. | 128/682 |
| 4,432,373 | 2/1984 | Ogawa et al. | 128/680 |

FOREIGN PATENT DOCUMENTS 49-35798  6/1974  Japan .................................. 128/680

*Primary Examiner*—Lee S. Cohen
*Assistant Examiner*—Angela D. Sykes
*Attorney, Agent, or Firm*—Frishauf, Holtz, Goodman & Woodward

[57] ABSTRACT

An electronic sphygmomanometer in which the gain of a Korotkoff sound amplifier for recognition of systolic blood pressure differs from that for recognition of diastolic blood pressure. A processor raises the amplifier gain upon recognizing systolic pressure, thereby establishing a mode for recognition of diastolic pressure. Alternatively, a trigger circuit, which produces a trigger signal in response to an input signal from the Korotkoff amplifier, has its threshold level set by the processor to a first value for recognition of systolic pressure and to lower second value for recognition of diastolic pressure, the lower second value being established following recognition of the systolic pressure.

6 Claims, 8 Drawing Figures

ELECTRONIC SPHYGMOMANOMETER

BACKGROUND OF THE INVENTION

1. Field of the Invention

This invention relates to an electronic sphygmomanometer and, more particularly, to an electronic sphygmomanometer for measuring blood pressure by electronically detecting the tapping sounds of arterial blood flow, or so-called Korotkoff sounds.

2. Description of the Prior Art

An electronic sphygmomanometer of the above type detects the Korotkoff sounds by a sensitive microphone or pressure sensor and applies the detected signal to a filter and amplifier unit of the required band width to obtain a signal of the kind shown in FIG. 1, in which A and B denote the electrical pulses representative of the systolic and diastolic Korotkoff tapping sounds, respectively. It is general practice to establish a certain threshold level with respect to the signal shown in FIG. 1 and to adopt an arrangement in which only pulses that exceed the threshold level are recognized.

In general, there is neither an abrupt increase in the magnitude of the Korotkoff pulse signal near the systolic pressure, nor is there an abrupt decrease in magnitude near the diastolic pressure. As a result, there are likely to be errors in reading the systolic and diastolic pressures, which errors are ascribable to the threshold level, as well as great differences in signal strength depending upon the individual whose blood pressure is being measured. Hence the accuracy of the sphygmomanometer is decided by the threshold level setting, or by the setting of the amplifier gain. Errors in the values measured by the prior-art electronic spyhgmomanometer occur to a marked degree in the vicinity of the diastolic pressure where the difference in signal level with respect to noise is small, and generally there is poor correlation with stethoscopy applied to detect the diastolic pressure.

Accordingly, since the magnitude of the Korotkoff sound signal differs depending upon the individual or in accordance with the conditions of measurement, a system has previously been proposed in Japanese patent application Laid-Open No. 55-122534 which takes into account the fact that errors in blood pressure measurement occur when a fixed level is employed for discrimination purposes. In the previously proposed arrangement, a circuit is provided, apart from a Korotkoff sound detecting circuit, for discriminating the Korotkoff signal level by means of a prescribed threshold level, and an AGC (automatic gain control) system is used to lower amplifier gain or to switch the threshold level when the Korotkoff signal level exceeds a predetermined value. With such an arrangement, however, amplifier gain for recognition of systolic pressure is the same as that for recognition of diastolic pressure if the input Korotkoff signal is small in magnitude or the signal level of the first detected arterial pulse is smaller than the predetermined value. Discrete levels thus cannot be set to conform to the differences which appear in the Korotkoff sound waveform at the systolic and diastolic pressures, and it is difficult to obtain a correct correlation with the measurement of diastolic pressure by means of stethoscopy.

With the above-described electronic sphygmomanometer, amplifier gain is lowered or the threshold level raised in response to a high Korotkoff signal level, but this is often a disadvantage since the gain for recognition of the diastolic pressure is not always raised to a value higher than that for recognition of the systolic pressure, thereby causing the diastolic pressure to be measured as being higher than the correct value (as measured by stethoscopy).

SUMMARY OF THE INVENTION

Accordingly, a general object of the present invention is to provide an electronic sphygmomanometer in which either the signal level or threshold level is set to the value best suited for measuring both the systolic and diastolic blood pressures, thereby enabling detection of Korotkoff sounds with greater accuracy than possible with the conventional electronic sphygmomanometer and affording good correlation with stethoscopy.

A more specific object of the present invention is to provide an electronic sphygmomanometer in which the gain of a Korotkoff amplifier or the threshold level of a trigger circuit is changed upon completion of the systolic pressure measurement, whereby the systolic and diastolic pressures are measured at the correct values thereof, as determined by stethoscopy.

Another object of the present invention is to provide a highly reliable electronic sphygmomanometer in which the gain or threshold level will not be set erroneously on account of noise.

According to the present invention, the foregoing and other objects are attained by providing an electronic sphygmomanometer which comprises an inflatable cuff having transducing means for producing electrical Korotkoff pulses indicative of Korotkoff tapping sounds, a Korotkoff pulse amplifier for amplifying the Korotkoff pulses, a trigger circuit for producing an output pulse upon being triggered by an amplified Korotkoff pulse input thereto from the Korotkoff pulse amplifier, a pressure detector, connected to the cuff, for producing an output signal indicative of the cuff pressure, a processor for reading in the output signal of the pressure detector in order to recognize systolic and diastolic pressure, and gain setting means for setting a first gain of the Korotkoff pulse amplifier for recognition of systolic pressure, and for setting a second gain of the Korotkoff pulse amplifier for recognition of diastolic pressure, the processor controlling the gain setting means in such a manner that the second gain of the Korotkoff pulse amplifier is set, following recognition of systolic pressure, to a value suitable for recognition of diastolic pressure. The gain setting means of the electronic sphygmomanometer includes first gain setting means adapted to set the gain of the Korotkoff pulse amplifier to the first gain for recognition of systolic pressure, and second gain setting means adapted to set the gain of the Korotkoff pulse amplifier to the second gain for recognition of diastolic pressure, and in which there are provided switching means, operable in response to a signal produced by the processor upon recognition of systolic pressure, for disconnecting the first gain setting means from the Korotkoff pulse amplifier and connecting the second gain setting means to the Korotkoff pulse amplifier. The gain setting means is adapted to set the second gain, for recognition of diastolic pressure, to a value higher than that of the first gain for recognition of systolic pressure. The processor recognizes as the systolic pressure the blood pressure which prevails when the trigger circuit produces at least a second of the output pulses within a predetermined time interval, and recognizes as the diastolic pressure the blood pressure which prevails when the last output pulse is produced by the trigger circuit, namely at such time that an output pulse from the trigger circuit is not followed by another output pulse within the time interval.

In accordance with another aspect of the present invention, there is provided an electronic sphygmomanometer which comprises an inflatable cuff having transducing means for producing electrical Korotkoff pulses indicative of Korotkoff tapping sounds, a Korotkoff pulse amplifier for amplifying the Korotkoff pulses, a trigger circuit for producing an output pulse upon being triggered by an amplified Korotkoff pulse input thereto from the Korotkoff pulse amplifier, a pressure detector, connected to the cuff, for producing an output signal indicative of the cuff pressure, a processor for reading in the output signal of the pressure detector in order to recognize systolic and diastolic pressure, and threshold level setting means for setting the threshold of the trigger circuit, with respect to the input signal thereto, to a first threshold level for recognition of systolic pressure and to a second threshold level for recognition of diastolic pressure, the processor controlling the threshold level setting means in such a manner that the second threshold level of the trigger circuit is set, following recognition of systolic pressure, to a value suitable for recognition of diastolic pressure. The threshold setting means of the electronic sphygmomanometer includes first threshold level setting means adapted to set the threshold of the trigger circuit to the first threshold level for recognition of systolic pressure, and second threshold level setting means adapted to set the threshold of the trigger circuit to the second threshold level for recognition of diastolic pressure, and in which there are provided switching means, operative in response to a signal produced by the processor upon recognition of systolic pressure, for disconnecting the first threshold level setting means from the trigger circuit and connecting the second threshold level setting means to the trigger circuit. The threshold level setting means is adapted to set the second threshold level, for recognition of diastolic pressure, to a value lower than that of the first threshold level for recognition of systolic pressure. The processor recognizes as the systolic pressure the blood pressure which prevails when the trigger circuit produces at least a second of the output pulses within a predetermined time interval, and recognizes as the diastolic pressure the blood pressure which prevails when the last output pulse is produced by the trigger circuit, namely at such time that an output pulse from the trigger circuit is not followed by another output pulse within the time interval.

Other features and advantages of the invention will be apparent from the following description taken in conjunction with the accompanying drawings in which like reference characters designate the same or similar parts throughout the figures thereof.

BRIEF DESCRIPTION OF THE DRAWINGS

FIG. 3 is a waveform diagram of signals associated with the arrangement of FIG. 2;

DESCRIPTION OF THE PREFERRED EMBODIMENT

Figure 1:
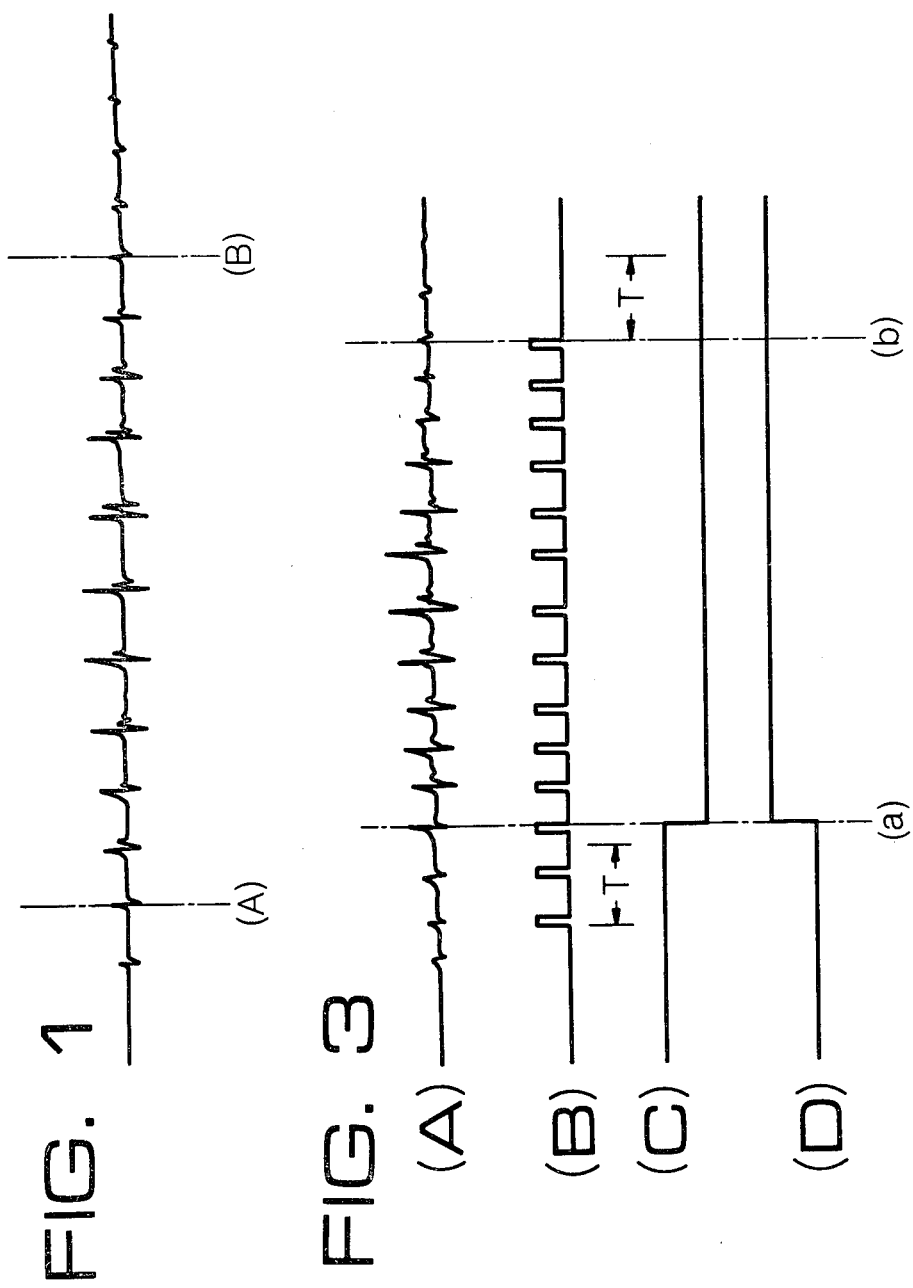
FIG. 1 is a waveform diagram of a Korotkoff signal.
Figure 2:
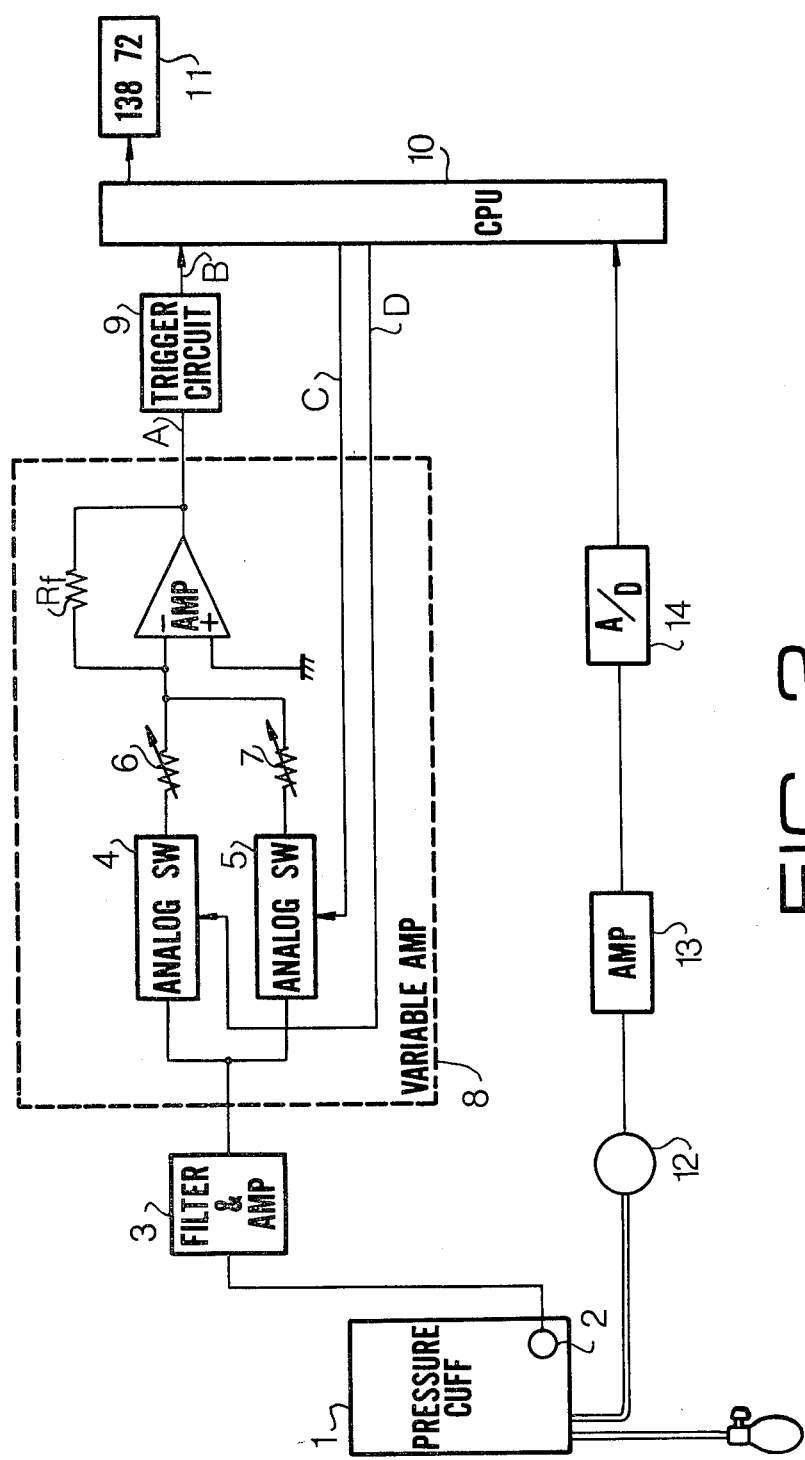
FIG. 2 is a block diagram illustrating a first embodiment of the present invention.

Referring to FIG. 2, a inflated cuff 1 is provided with transducing means such as a microphone 2. The inflated cuff 1, normally applied to the upper arm, is inflated to a prescribed pressure to occlude arterial blood flow, with the microphone 2 serving to detect the Korotkoff tapping sounds when the air pressure is relieved. The output of the microphone 2 is applied to a filter and amplifier unit 3 where the signal of the required band width is amplified and when delivered to a variable gain amplifier 8. The variable gain amplifier 8 is composed of first means comprising an analog switch 5 and rheostat 7 for setting the gain of an amplifier AMP to a value for recognition of systolic pressure, and second means comprising an analog switch 4 and rheostat 6 for setting the gain of the amplifier AMP to a value for recognition of diastolic pressure. The analog switches 5, 4 of the variable gain amplifier 8 initially are in the ON and OFF states, respectively, in response to high- and low-level signals C, D from a CPU (microprocessor) 10. Here the resistance of rheostat 7 is set to be higher than that of rheostat 6. Such a condition enables the gain of the amplifier to be set low for recognition of the systolic blood pressure. It should be noted that the resistor Rf in FIG. 2 is a feedback resistor which decides the gain of the variable gain amplifier 8 in cooperation with the rheostats 6, 7.

The amplified, pulsed output A of variable gain amplifier 8, namely the electrical Korotkoff signal shown in (A) of FIG. 3, is applied to a trigger circuit 9 which is triggered thereby to convert the signal into the pulse train shown in (B) of FIG. 3, the pulse train being applied to the CPU 10. In FIG. 3, a denotes confirmation of systolic pressure, and b confirmation of diastolic pressure. Returning to FIG. 2, the cuff 1 is connected to a pressure detector 12 whose output, indicative of the cuff pressure, is applied to an A/D converter following amplification by means of an amplifier 13. The A/D converter 14 converts the analog pressure signal from amplifier 13 into a digital signal which is read in by the CPU 10.

Figure 4:
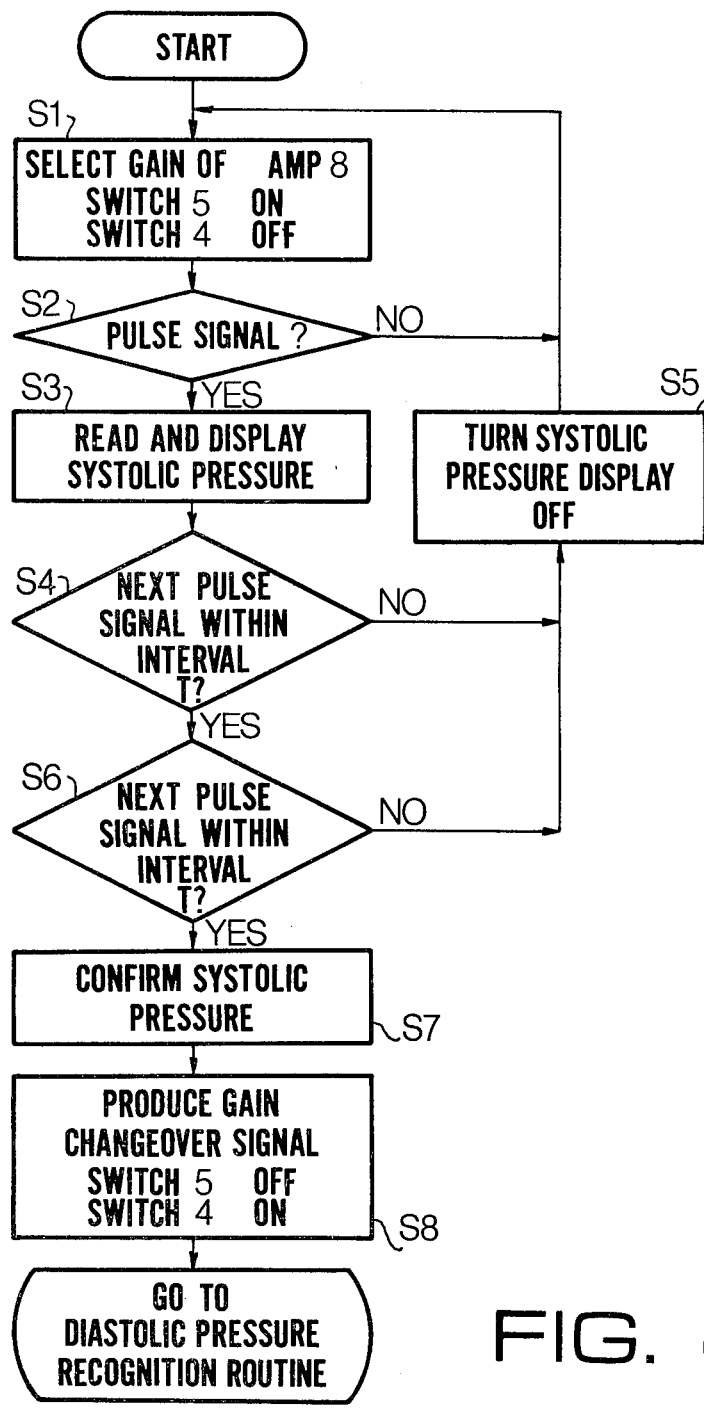
FIG. 4 is a flow chart of a systolic pressure recognition routine in the first embodiment of the present invention.
Figure 5:
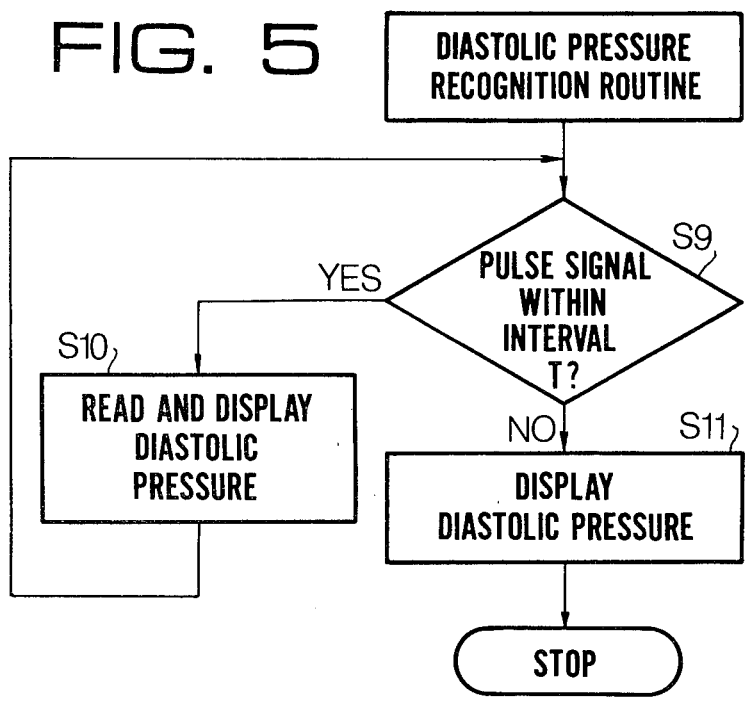
FIG. 5 is a flow chart of a diastolic pressure recognition routine in the first embodiment of the present invention.

Reference will now be had to FIGS. 4 and 5 to describe the routines for recognizing systolic and diastolic pressure.

First, it should be noted that a program for systolic and diastolic pressure recognition is loaded in a read-only memory (not shown) located within the CPU 10. The program starts following inflation of the cuff 1 when the CPU 10 senses, via the pressure detector 12, amplifier 13 and A/D converter 14, that the cuff has been pressurized beyond a specified value. The first step S1 in the routine is for analog switch 5 to be turned ON and analog switch 4 to be turned OFF in response to the signals C, D from the CPU 10, whereby the gain of variable amplifier 8 is so set as to recognize the systolic pressure. In step S2, the CPU senses whether the pulse signal of FIG. 3(B) has been produced by the trigger circuit 9 upon the gradual deflation of the cuff 1 achieved by slowly bleeding the air therefrom. If a pulse is detected, processing shifts to step S3 in which the CPU 10 reads the magnitude of the currently prevailing output of the pressure detector 12 through the amplifier 13 and A/D converter 14 and causes the read value, namely the systolic pressure, to be displayed by means of the display device 11.

Next, in step S4, the CPU determines whether the first detected pulse in pulse train (B) has been followed by another within a predetermined time interval T. If it has not, the first pulse is treated as being a noise pulse, the display of systolic pressure is extinguished, and the initial conditions are restored, whereupon blood pressure measurement is resumed by deflating the cuff 1. This is the processing indicated by step S5. If the CPU 10 detects that the first pulse is indeed followed by a pulse within the interval T in step S4, then processing shifts to step S6 where the operation performed in step S4 is repeated. That is, if a subsequent pulse is not detected within the interval T, operation thus far is treated as being the result of noise and, in step S5, the display of systolic pressure is cancelled and the initial conditions restored. If a subsequent pulse is present within the interval T, however, then the systolic pressure reading is confirmed in step S7 (at a in FIG. 3) and processing shifts to step S8, in which the CPU 10 switches the gain of the variable gain amplifier 8.

Thus, the arrangement according to the first embodiment of the present invention is such that the magnitude of the systolic pressure is recognized only when the Korotkoff tapping sounds have been detected for three pulses in succession. Upon confirmation of the systolic pressure value, the CPU 10 switches the potential levels of the signals C, D, with signal C going low and signal D high to turn analog switch 5 OFF and analog switch 4 ON, whereby processing shifts to the routine for confirming diastolic pressure, as illustrated in FIG. 5. Here the gain of the variable gain amplifier is set by the rheostat 6 until confirmation of the diastolic pressure. And since the resistance of rheostat 6 is less than that of reheostat 7, as mentioned above, the gain of the variable gain amplifier will be set high.

With reference now to the diastolic pressure recognition flow chart of FIG. 5, in step S9 the CPU 10 examines the pulses in the pulse train B from the trigger circuit 9 to determine whether a pulse is followed by another within the specified time interval T. If a pulse is sensed to follow another within said time interval, the prevailing blood pressure is read and displayed by the CPU 10 in step S10. If not, then the last read value of the blood pressure (at b in FIG. 3) is displayed on the display device 11 as the diastolic pressure. This is step S11, and completes the blood pressure measurement. In order to perform the next measurement operation, the gain of the amplifier must be reset to the gain for systolic pressure measurement. A preferred arrangement for accomplishing this would be to have the CPU 10 establish the reset condition when the pressure detector 12 detects repressurization of the cuff 1.

Figure 6:
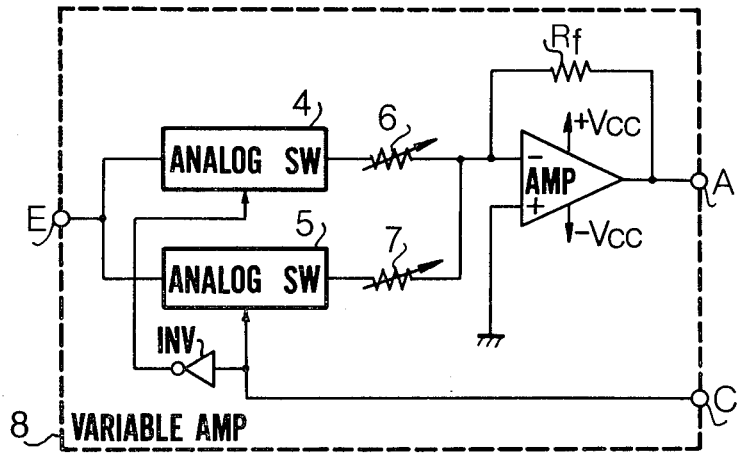
FIG. 6 is a block diagram illustrating a modification of a gain control circuit for a variable gain amplifier.

A modification of the gain control circuit of variable gain amplifier 8 is illustrated in FIG. 6, in which the output signal C of the CPU 10 is applied to the analog switch 4 through an inverter INV, in place of the signal D described above in connection with FIG. 2. In this arrangement, therefore, the CPU 10 need provide only the single control signal C which, since it is inverted before entering the analog switch 4, establishes the same conditions as the signals C and D in FIG. 2.

Figure 7:
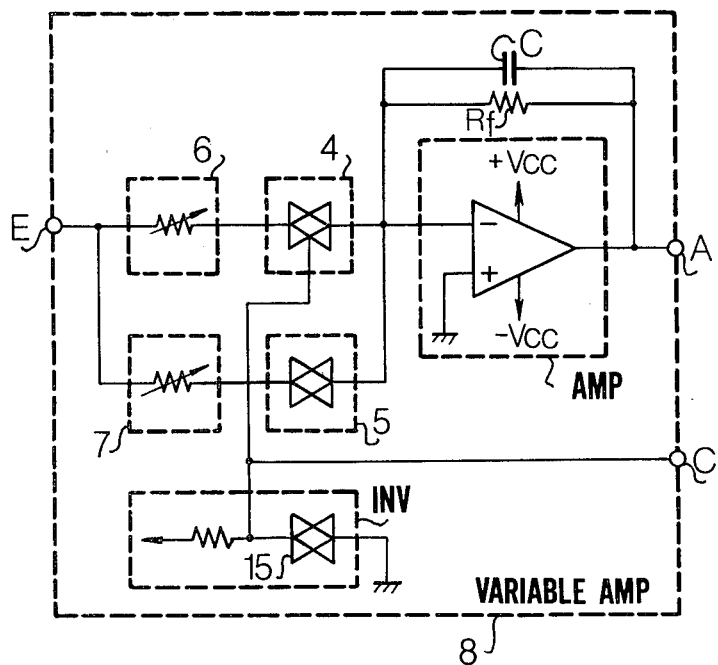
FIG. 7 is a circuit diagram showing the arrangement of FIG. 6 in greater detail.

A more detailed circuit diagram exemplifying the arrangement of FIG. 6 is shown in FIG. 7, in which like reference characters denote the same or corresponding parts. In FIG. 7, the inverter INV includes a switch 15 that is turned ON when the control signal C goes high, thereby connecting the analog switch 4 to ground so that the switch 4 is turned OFF. Conversely, when the control signal C is low, the inverter INV turns the analog switch 4 ON by connecting it to a potential of $+V_{cc}$. It will also be noted that a capacitor C is connected in parallel with the resistor Rf to form an integrator for the purpose of removing noise.

It will be appreciated from the foregoing description that the gain of the variable gain amplifier 8 can be set to one value for recognition of systolic pressure, and to another value for recognition of diastolic pressure, and that the gain can be set high in the latter case, namely for recognition of the diastolic pressure. In other words, according to the above-described embodiment of the present invention, the gain for recognition of both the systolic and diastolic pressures can be set to the value best suited for the particular threshold level of the Korotkoff signal. It should be noted, however, that the equivalent of setting the gain of the variable gain amplifier 8 would be to changeover the threshold level of the trigger circuit 9, thereby providing an alternative method of achieving the foregoing effects. This will be described in further detail with reference to FIG. 8.

Figure 8:
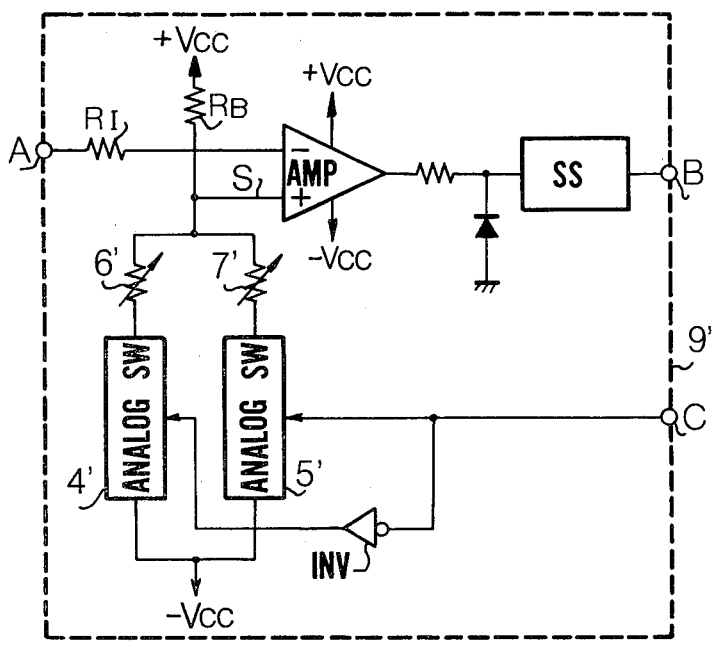
FIG. 8 is a block diagram illustrating a second embodiment of the present invention.

FIG. 8 illustrates a circuit for varying the threshold level of the trigger circuit 9 in accordance with a second embodiment of the present invention. Here the output A of the preceding amplifier stage is fixed and applied to an amplifier AMP' of an open loop, with the arrangement being such that the threshold level is set to one level for recognizing systolic pressure, and to a second level for recognizing diastolic pressure, in response to the control signal C from the CPU 10. More specifically, analog switches 4', 5' are connected to the positive input of the amplifier AMP' through rheostats 6', 7', the negative input to the amplifier receiving the output A of the previous stage. The control signal C from the CPU 10 is applied directly to the analog switch 5', and to the analog switch 4' through an inverter INV'. A resistor $R_B$ is connected between $+V_{cc}$ and the junction of rheostats 6', 7'. When the control signal C is set high for recognition of systolic pressure, analog switch 5' is turned ON, and analog switch 4' is turned OFF. Thus, a first threshold level S, which is decided by the dividing ratio of the rheostat 7' and resistor $R_B$, can be preset so as to attain the optimum value for systolic pressure recognition. It goes without saying that the threshold level S at this time is higher than a second threshold level S' which will be established in order to recognize the diastolic pressure. When the measurement of systolic pressure is completed, the CPU 10 reverses the potential level of the control signal C, thereby turning analog switch 5' OFF and analog switch 4' ON. Here the dividing ratio decided by the resistor $R_B$ and rheostat 6' is so preset as to assure that the threshold level which prevails under these conditions will assume the optimum value.

In FIG. 8, the output of the amplifier AMP' is connected to a monostable multivibrator SS through a resistor to construct a trigger circuit 9' in which, when the input signal to the amplifier AMP' exceeds the threshold value, the monostable multivibrator SS is triggered by the leading edge of the amplifier output. Such an arrangement allows the CPU 10 to be supplied with the pulses B of a constant pulse width. The circuit arrangement is similar to that of FIG. 2.

It will be appreciated from the foregoing discussion that lowering the threshold level for recognition of diastolic pressure corresponds to raising the gain of the amplifier 8, which was described earlier, and that raising the threshold level is equivalent to lowering the gain of the amplifier. Also, control of the analog switches 4', 5' executed by the CPU 10 in the embodiment of FIG. 8 may be understood from the flow charts of FIGS. 4 and 5 by substituting the word "threshold" for the word "gain" in steps S1 and S8. For this reason, the processing routine for switching the threshold level need not be described again here.

The advantages and effects of the present invention, which is constructed and which operates in the manner described hereinabove, will now be set forth.

In accordance with the first preferred embodiment of the present invention, the gain of the Korotkoff signal amplifier is set to one value for recognition of systolic pressure and to a second value for recognition of diastolic pressure. After detection of systolic pressure is confirmed, the gain is switched over to the second value, which is suitable for measurement of diastolic pressure. This value of the gain is greater than the first value. This enables both the systolic and diastolic pressure values to be measured while providing accurate correlation with stethoscopy. More specifically, since amplifier gain is set low only for recognition of systolic pressure, the magnitude of the systolic pressure will not be measured as being higher than the correct value, owing to an excessively high amplifier gain. Likewise, since the gain is set high for recognition of diastolic pressure, the magnitude of the diastolic pressure will not be measured as being higher than the correct value, owing to insufficient amplifier gain.

Another advantage of the invention is excellent removal of noise by reason of the fact that amplifier gain is controlled through use of a processor. Thus there is a very low incidence of noise-induced erroneous operation.

In accordance with the second preferred embodiment of the present invention, the threshold level is set to one value for detection of systolic pressure and to a second value for detection of diastolic pressure, with the threshold level being set to the second, or lower, value after confirmation of the systolic pressure. This corresponds to the raise in amplifier gain described above. Thus, whereas the first embodiment takes the approach of providing a low gain for systolic pressure recognition and a high gain for diastolic pressure recognition, the second embodiment sets the threshold level high for the former case and low for the latter. The advantages and effects of the second embodiment, therefore, are as pointed out above.

While the analog switches employed in the foregoing embodiments typically are field-effect transistors, other switching means such as transistor switches, relays and the like may be used.

As many apparently widely different embodiments of the present invention can be made without departing from the spirit and scope thereof, it is to be understood that the invention is not limited to the specific embodiments thereof except as defined in the appended claims.

What is claimed is:

1. An electronic sphygmomanometer which comprises:
    an inflatable cuff having transducing means for producing electrical Korotkoff pulses indicative of Korotkoff tapping sounds, said cuff being inflatable over a pressure range including systolic and diastolic pressures to be measured;
    a Korotkoff pulse amplifier which amplifies the Korotkoff pulses from said transducing means;
    a trigger circuit coupled to said Korotkoff pulse amplifier, which produces an output pulse upon being triggered by an amplified Korotkoff pulse input thereto from said Korotkoff pulse amplifier;
    a pressure detector, connected to said cuff, which produces an output signal indicative of the cuff pressure;
    a processor coupled to said trigger circuit and to said pressure detector, which reads in the output signal of said pressure detector in order to recognize systolic and diastolic pressure; and
    gain setting means coupled to said processor for setting a first gain of said Korotkoff pulse amplifier for recognition of systolic pressure, and for setting a second gain of said Korotkoff pulse amplifier for recognition of diastolic pressure;
    wherein said processor includes means for recognizing as the systolic pressure the cuff pressure which prevails when said trigger circuit produces at least a second output pulse within a predetermined time interval and, after the systolic pressure is recognized, to control said gain setting means to set the second gain larger than the first gain and to recognize as the diastolic pressure the cuff pressure which prevails when an output pulse from said trigger circuit is not followed by another output pulse within said time interval.

2. An electronic sphygmomanometer according to claim 1, in which said gain setting means includes first gain setting means for setting the gain of said Korotkoff pulse amplifier to said first gain for recognition of systolic pressure, and second gain setting means for setting the gain of said Korotkoff pulse amplifier to said second gain for recognition of diastolic pressure, and in which there are provided switching means, responding to a signal produced by said processor upon recognition of systolic pressure, for disconnecting said first gain setting means from said Korotkoff pulse amplifier and connecting said second gain setting means to said Korotkoff pulse amplifier.

3. An electronic sphygmomanometer according to claim 1, in which said gain setting means sets said second gain, for recognition of diastolic pressure, to a value higher than that of said first gain for recognition of systolic pressure.

4. An electronic sphygmomanometer which comprises:
    an inflatable cuff having transducing means for producing electrical Korotkoff pulses indicative of Korotkoff tapping sounds, said cuff being inflatable over a pressure range including systolic and diastolic pressures to be measured;
    a Korotkoff pulse amplifier which amplifies the Korotkoff pulses from said transducing means;
    a trigger circuit coupled to said Korotkoff pulse amplifier, which produces an output pulse on being triggered by an amplified Korotkoff pulse input thereto from said Korotkoff pulse amplifier;

a pressure detector, connected to said cuff, which produces an output signal indicative of the cuff pressure;

a processor coupled to said trigger circuit and to said pressure detector, which reads in the output signal of said pressure detector in order to recognize systolic and diastolic pressure; and threshold level setting means coupled to said processor for setting the threshold of said trigger circuit, with respect to the input signal thereto from said Korotkoff pulse amplifier, to a first threshold level for recognition of systolic pressure and to a second threshold level for recognition of diastolic pressure;

said processor including means for recognizing as the systolic pressure the cuff pressure which prevails when said trigger circuit produces at least a second output pulse within a predetermined time interval and, after the systolic pressure is recognized, to control said threshold level setting means to set the second threshold level lower than the first threshold level, and to recognize as the diastolic pressure the cuff pressure which prevails when an output pulse from said trigger circuit is not followed by another output pulse within said time interval;

wherein said processor controls said threshold level setting means in such a manner that the second threshold level of said trigger circuit is set, following recognition of systolic pressure, to a value suitable for recognition of diastolic pressure.

5. An electronic sphygmomanometer according to claim 4, in which said threshold level setting means includes first threshold level setting means for setting the threshold of said trigger circuit to said first threshold level for recognition of systolic pressure, and second threshold level setting means for setting the threshold of said trigger circuit to said second threshold level for recognition of diastolic pressure, and in which there are provided switching means, responding to a signal produced by said processor upon recognition of systolic pressure, for disconnecting said first threshold level setting means from said trigger circuit and connecting said second threshold level setting means to said trigger cicuit.

6. An electronic sphygmomanometer according to claim 4, in which said threshold level setting means sets said second threshold level, for recognition of diastolic pressure, to a value lower than that of said first threshold level for recognition of systolic pressure.

* * * * *